(12) United States Patent
DeVries et al.

(10) Patent No.: US 6,410,750 B1
(45) Date of Patent: Jun. 25, 2002

(54) PROCESSES AND INTERMEDIATES FOR PREPARING 3(S)-[(5-CHLORO-1H-INDOLE-2-CARBONYL)-AMINO]-2(R)-HYDROXY-4-PHENYL-BUTYRIC ACID

(75) Inventors: Keith M. DeVries, Chester; Darrell E. Fox, Pawcatuck; Philip D. Hammen, East Haddam; Dennis J. Hoover, Mystic, all of CT (US); Jeffrey B. Jorgensen, Nashville, TN (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/565,523

(22) Filed: May 5, 2000

Related U.S. Application Data

(60) Provisional application No. 60/139,997, filed on Jun. 18, 1999.

(51) Int. Cl.[7] ............................................. C07D 209/20
(52) U.S. Cl. ...................................................... 548/492
(58) Field of Search .......................................... 548/492

(56) References Cited

FOREIGN PATENT DOCUMENTS

| WO | WO9639384 | 12/1996 |
|----|-----------|---------|
| WO | WO9639385 | 12/1996 |

*Primary Examiner*—Laura L. Stockton
(74) *Attorney, Agent, or Firm*—Peter C. Richardson; Gregg C. Benson; Jennifer A. Kispert

(57) ABSTRACT

The present invention provides novel processes for preparing 3(S)-[(5-chloro-1H-indole-2-carbonyl)-amino]-2(R)-hydroxy-4-phenyl-butyric acid. Also provided are novel intermediates used in those processes. Further, the 3(S)-[(5-chloro-1H-indole-2-carbonyl)-amino]-2(R)-hydroxy-4-phenyl-butyric acid prepared by the novel processes can be further reacted to yield known indole 2-carboxamides and derivatives thereof possessing glycogen phosphorylase inhibitory activity, which are useful in the treatment of mammals, especially human beings, having glycogen phosphorylase dependent diseases or conditions.

22 Claims, No Drawings

PROCESSES AND INTERMEDIATES FOR PREPARING 3(S)-[(5-CHLORO-1H-INDOLE-2-CARBONYL)-AMINO]-2(R)-HYDROXY-4-PHENYL-BUTYRIC ACID

CROSSREFERENCE TO RELATED APPLICATION

This application claims priority from U.S. Provisional Patent Application No. 60/139,997 filed Jun. 18, 1999, the benefit of which is hereby claimed under 37 C.F.R. §1.78 (a)(3).

FIELD OF THE INVENTION

The present invention relates to novel processes for preparing 3(S)-[(5-chloro-1H-indole-2-carbonyl)-amino]-2(R)-hydroxy-4-phenyl-butyric acid, which can be further reacted to form compounds which possess glycogen phosphorylase inhibitory activity. Also provided are novel intermediates used in those processes. These glycogen phosphorylase inhibitors are useful in the treatment of mammals, especially human beings, having glycogen phosphorylase dependent diseases or conditions including hypercholesterolemia, hyperglycemia, hyperinsulinemias, hyperlipidemia, hypertension, atherosclerosis, diabetes and myocardial ischemia.

BACKGROUND OF THE INVENTION

International PCT Application Numbers PCT/IB95/00443 published as WO 96/39385 and PCT/IB95/00442 published as WO 96/39384, counterpart U.S. Pat. No. 6,107,329, disclose novel substituted N-(indole-2-carbonyl)-amides, derivatives and intermediates including 3(S)-[(5-chloro- I H-indole-2-carbonyl)-amino]-2(R)-hydroxy-4-phenyl-butyric acid, processes for preparing such compounds, pharmaceutical compositions comprising such compounds or derivatives, and methods of treating glycogen phosphorylase dependent diseases or conditions by administering such compounds or derivatives.

As disclosed thereby, 3(S)-[(5-chloro-1H-indole-2-carbonyl)-amino]-2(R)-hydroxy-4-phenyl-butyric acid can be prepared by coupling an acid chloride with an amino acid to yield an ester of 3(S)-[(5-chloro-1H-indole-2-carbonyl)-amino]-2(R)-hydroxy-4-phenyl-butyric acid, which can then be deprotected by aqueous alkaline hydrolysis to yield the corresponding acid.

The present invention provides novel processes for preparing 3(S)-[(5-chloro-1H-indole-2-carbonyl)-amino]-2(R)-hydroxy-4-phenyl-butyric acid which utilize two fewer steps than the prior art processes referred to above which, in turn, provides for a quicker, easier and less costly method of production. The presently disclosed processes generate as few as two intermediates which need not be isolated, and a single isolation provides 3(S)-[(5-chloro-1H-indole-2-carbonyl)-amino]-2(R)-hydroxy-4-phenyl-butyric acid. Further, this product need not be isolated either, i.e., it may be carried on, as disclosed, for example, in the aforementioned WO 96/39385 and/or WO 96/39384, to form glycogen phosphorylase inhibitors disclosed therein.

All of the documents cited herein, including the foregoing, are incorporated by reference herein in their entireties.

SUMMARY OF THE INVENTION

The present invention relates to novel processes for preparing 3(S)-[(5-chloro-1H-indole-2-carbonyl)-amino]-2(R)-hydroxy-4-phenyl-butyric acid.

The present invention also relates to novel intermediates generated during the processes of this invention.

In a first aspect, this invention provides processes for preparing 3(S)-[(5-chloro-1H-indole-2-carbonyl)-amino]-2(R)-hydroxy-4-phenyl-butyric acid, the compound of Formula 6

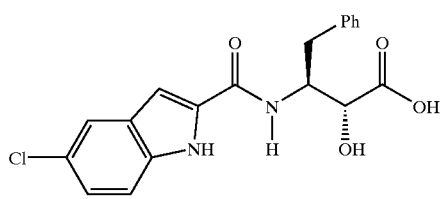

6 which comprise the steps of:
preparing a solution comprising the compound of Formula 2

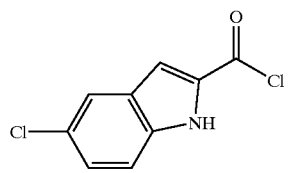

2 comprising, in sequence, adding the compound of Formula 1

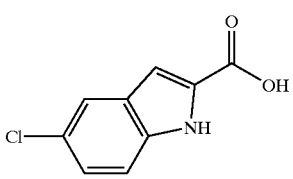

1 to an aprotic solvent A, adding an amount of a catalytic aprotic solvent with agitation under an inert gas, and adding an activating agent;
preparing the compound of Formula 4

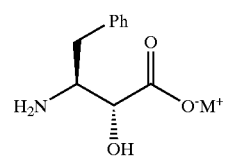

4 where M$^+$ is any monovalent cation from the compound of Formula 3

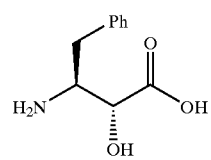

3 comprising, in sequence, adding the compound of Formula 3 and a base to a mixture of an aprotic solvent B and a protic solvent, at a temperature of from about −20° C. to about the reflux temperature of said mixture, and maintaining the pH of said mixture at from about pH 8 to about pH 13;

preparing the compound of Formula 5 by coupling said compounds of Formulae 2 and 4

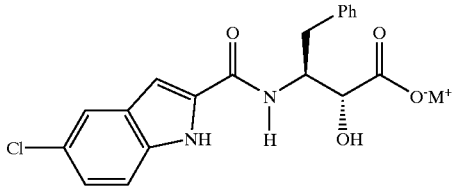

comprising, in sequence, adding said solution to said mixture, under an inert gas, while maintaining said temperature and, after said addition is complete, allowing said mixture to reach room temperature;

adding an amount of an organic solvent to said mixture; and extracting said compound of Formula 6 into said organic solvent comprising, in sequence, separating the aqueous layer A and the organic layer A, treating said organic layer A with an aqueous acid solution, or with an aqueous acid solution and $H_2O$, separating the aqueous layer B from the organic layer B, and retaining said organic layer B;

provided that, when $M^+$ is $N(C_1-C_6\ alkyl)_4^+$, tetra-$C_1-C_6$ alkylammonium halide is added to said mixture after said base.

In a preferred embodiment of said first aspect, said aprotic solvent A and said aprotic solvent B are each independently THF, toluene, or $CH_2Cl_2$. Aprotic solvent A and aprotic solvent B are each preferably toluene.

In another preferred embodiment of said first aspect, said catalytic aprotic solvent is DMF.

In another preferred embodiment of said first aspect, said inert gas is $N_2$.

In another preferred embodiment of said first aspect, said activating agent is oxalyl chloride or thionyl chloride. Thionyl chloride is a particularly preferred activating agent. In a preferred embodiment wherein said activating agent is thionyl chloride, said addition is completed after about 16 h.

In another preferred embodiment of said first aspect, said $M^+$ is $Li^+$, $Na^+$, $K^+$, $Cs^+$ or tetra-$C_1-C_6$ alkylammonium. A particularly preferred $M^+$ is $Na^+$, $K^+$, or $NBu_4^+$. An especially preferred $M^+$ is $K^+$. A particularly preferred tetra-$C_1-C_6$ alkylammonium halide is TBAB.

In another preferred embodiment of said first aspect, said base is sodium bicarbonate, sodium hydroxide, sodium phosphate, potassium carbonate, dibasic potassium phosphate or tribasic potassium phosphate. Particularly preferred bases include sodium bicarbonate, potassium bicarbonate and tribasic potassium phosphate. Tribasic potassium phosphate is an especially preferred base. In a preferred embodiment wherein said base is potassium carbonate, said $M^+$ is $NBu_4^+$ and said tetra-$C_1-C_6$ alkylammonium halide is TBAB. In a preferred embodiment wherein said base is sodium bicarbonate, said $M^+$ is $Na^+$. In a preferred embodiment wherein said base is sodium bicarbonate and said $M^+$ is $Na^+$, said aprotic solvent B is THF, said protic solvent is $H_2O$, and said temperature is about 65° C. In a preferred embodiment wherein said base is tribasic potassium phosphate, said $M^+$ is $K^+$. In a preferred embodiment wherein said base is tribasic potassium phosphate and said $M^+$ is $K^+$, said aprotic solvent B is THF, said protic solvent is $H_2O$, and said temperature is about −5° C.

In another preferred embodiment of said first aspect, said protic solvent is $H_2O$ or ROH where R is $C_1-C_4$ alkyl.

Particularly preferred protic solvents include $H_2O$ and MeOH. An especially preferred protic solvent is $H_2O$.

In another preferred embodiment of said first aspect, said pH is maintained by said base.

In another preferred embodiment of said first aspect, said pH is from about pH 11 to about pH 13.

In another preferred embodiment of said first aspect, said organic solvent is EtOAc or $CH_2Cl_2$. A particularly preferred organic solvent is $CH_2Cl_2$.

In another preferred embodiment of said first aspect, said aqueous acid solution is aqueous HCl or aqueous $H_2SO_4$. A particularly preferred aqueous acid solution is aqueous HCl.

In another preferred embodiment of said first aspect, said retained organic layer B is concentrated, displaced into hexanes or heptanes, granulated in said hexanes or said heptanes for a period of time under an inert gas, and the resultant slurry is filtered and the retenate (comprising the compound of Formula 6) is dried. A preferred period of time is overnight. A preferred inert gas is $N_2$.

In another preferred embodiment of said first aspect, said compound of Formula 2 is isolated before its addition to said mixture, dissolved in an aprotic solvent C, and added to said mixture by adding said aprotic solvent C comprising said compound of Formula 2 to said mixture. A preferred method of isolation comprises, in sequence: adding hexanes or heptanes to said solution, filtering the resultant slurry and drying the retentate. Aprotic solvent C is preferably THF, toluene, or $CH_2Cl_2$, and is particularly preferably THF.

In a particularly preferred embodiment of said first aspect, said process for preparing said compound of Formula 6, comprises the steps of: preparing a solution comprising the compound of Formula 2 comprising, in sequence, adding the compound of Formula 1 to toluene, adding an amount of DMF with stirring under $N_2$, and adding $SOCl_2$; preparing the compound of Formula 4 wherein $M^+$ is $Na^+$ from the compound of Formula 3 comprising, in sequence, adding said compound of Formula 3 and $NaHCO_3$ to a mixture of THF and $H_2O$, at about 65° C.; preparing the compound of Formula 5 wherein $M^+$ is $Na^+$ by coupling said compounds of Formulae 2 and 4 comprising, in sequence, adding said solution to said mixture, under $N_2$, while maintaining about 65° C. and, after said addition is complete, allowing said mixture to reach RT; adding an amount of EtOAc to said mixture; extracting said compound of Formula 6 into said EtOAc comprising, in sequence: separating said aqueous layer A and said organic layer A, treating said organic layer A with an aqueous acid solution, separating said aqueous layer B from said organic layer B, and retaining said organic layer B; and isolating said compound of Formula 6 comprising, in sequence: concentrating said retained organic layer B, displacing said concentrated organic layer B into hexanes or heptanes, granulating said displaced organic layer B in said hexanes or heptanes overnight under $N_2$, filtering the resultant slurry, and drying the retentate.

In a particularly preferred embodiment of said first aspect, said process for preparing said compound of Formula 6, comprises the steps of: preparing a solution comprising the compound of Formula 2 comprising, in sequence, adding the compound of Formula 1 to toluene, adding an amount of DMF with stirring under $N_2$, and adding $SOCl_2$; preparing the compound of Formula 4 wherein $M^+$ is $K^+$ from the compound of Formula 3 comprising, in sequence, adding said compound of Formula 3 and $K_3PO_4$ to a mixture of THF and $H_2O$, at about −5° C.; preparing the compound of Formula 5 wherein $M^+$ is $K^+$ by coupling said compounds of Formulae 2 and 4 comprising, in sequence, adding said solution to said mixture, under $N_2$, while maintaining about −5° C. and, after said addition is complete, allowing said mixture to reach room temperature; adding an amount of CH₂Cl₂ to said mixture; extracting said compound of Formula 6 into said CH₂Cl₂ comprising, in sequence: separating said aqueous layer A and said organic layer A, treating said organic layer A with 1M HCl, separating said aqueous layer B from said organic layer B, and retaining said organic layer B; and isolating said compound of Formula 6 comprising, in sequence: concentrating said retained organic layer B by distillation, displacing said concentrated layer into heptanes or hexanes until the vapor temperature reaches about 95° C., cooling to ambient temperature, filtering the resultant slurry, and drying the retentate.

In a further particularly preferred embodiment of said first aspect, said compound of Formula 6 is further reacted to form substituted N-(indole-2-carbonyl)-amides and derivatives disclosed in the aforementioned WO 96/39385 and/or WO 96/39384 as described therein, e.g., using Procedure A (Peptide Coupling Using DEC).

For example, as disclosed in the aforementioned WO 96/39385, the compound of Formula 6 prepared by the novel processes of this invention may be further reacted to yield, e.g., 5-chloro-1H-indole-2-carboxylic acid [(1S)-((R)-hydroxy-dimethylcarbamoyl-methyl)-2-phenyl-ethyl]-amide, 5,6-dichloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid {(1S)-[(R)-hydroxy-(methoxy-methyl-carbamoyl)-methyl]-2-phenyl-ethyl}-amide, 5-chloro-1H-indole-2-carboxylic acid ((1S)-{(R)-hydroxy-[2-hydroxy-ethyl)-methyl-carbamoyl]-methyl}-2-phenyl-ethyl)-amide, 5-chloro-1H-indole-2-carboxylic acid {(1S)-[(R)-hydroxy-(methyl-pyridin-2-yl-carbamoyl)-methyl]-2-phenyl-ethyl}-amide, 5-chloro-1H-indole-2-carboxylic acid ((1S)-{(R)-hydroxy-[methyl-(2-pyridin-2-yl-ethyl)-carbamoyl]-methyl}-2-phenyl-ethyl)-amide, 5-chloro-1H-indole-2-carboxylic acid [(1S)-benzyl-(2R)-hydroxy-3-(4-methyl-piperazin-1-yl)-3-oxo-propyl]-amide hydrochloride, 5-chloro-1H-indole-2-carboxylic acid [(1S)-benzyl-(2R)-hydroxy-3-(3-hydroxy-azetidin-1-yl)-3-oxo-propyl]-amide, 5-chloro-1H-indole-2-carboxylic acid ((1S)-benzyl-(2R)-hydroxy-3-isoxazolidin-2-yl-3-oxo-propyl)-amide, 5-chloro-1H-indole-2-carboxylic acid ((1S)-benzyl-(2R)-hydroxy-3-[1,2]oxazinan-2-yl-3-oxo-propyl)-amide, 5-chloro-1H-indole-2-carboxylic acid [(1S)-benzyl-(2R)-hydroxy-3-((3S)-hydroxy-pyrrolidin-1-yl)-3-oxo-propyl]-amide, 5-chloro-1H-indole-2-carboxylic acid [(1S)-benzyl-3-((3S, 4S)-dihydroxy-pyrrolidin-1-yl)-(2R)-hydroxy-3-oxo-propyl]-amide, 5-chloro-1H-indole-2-carboxylic acid [(1S)-benzyl-3-((3R, 4S)-dihydroxy-pyrrolidin-1-yl)-(2R)-hydroxy-3-oxo-propyl]-amide or 5-chloro-1H-indole-2-carboxylic acid ((1S)-benzyl-(2R)-hydroxy-3-morpholin-4-yl-3-oxo-propyl)-amide.

As disclosed in the aforementioned WO 96/39384, the compound of Formula 6 prepared by the novel processes of this invention may be further reacted to yield, e.g., 5-chloro-1H-indole-2-carboxylic acid [(1S)-benzyl-2-(3-hydroxyimino-pyrrolidin-1-yl)-2-oxo-ethyl]-amide, 5-chloro-1H-indole-2-carboxylic acid [2-(cis-3,4-dihydroxy-pyrrolidin-1-yl)-2-oxo-ethyl]-amide, 5-chloro-1H-indole-2-carboxylic acid [2-((3S, 4S)-dihydroxy-pyrrolidin-1-yl)-2-oxo-ethyl]-amide, 5-chloro-1H-indole-2-carboxylic acid [(1S)-benzyl-2-(cis-3,4-dihydroxy-pyrrolidin-1-yl)-2-oxo-ethyl]-amide, 5-chloro-1H-indole-2-carboxylic acid [2-(1,1-dioxo-thiazolidin-3-yl)-2-oxo-ethyl]-amide, 5-chloro-1H-indole-2-carboxylic acid (2-oxo-2-thiazolidin-3-yl-ethyl)-amide, 5-chloro-1H-indole-2-carboxylic acid [(1S)-(4-fluoro-benzyl)-2-(4-hydroxy-piperidin-1-yl)-2-oxo-ethyl]-amide, 5-chloro-1H-indole-2-carboxylic acid [(1S)-benzyl-2-((3RS)-hydroxy-piperidin-1-yl)-2-oxo-ethyl]-amide, 5-chloro-1H-indole-2-carboxylic acid [2-oxo-2-((1 RS)-oxo-1-thiazolidin-3-yl)-ethyl]-amide, 5-chloro-1H-indole-2-carboxylic acid [(1S)-(2-fluoro-benzyl)-2-(4-hydroxy-piperidin-1-yl)-2-oxo-ethyl]-amide, 5-chloro-1H-indole-2-carboxylic acid [(1S)-benzyl-2-((3S, 4S)-dihydroxy-pyrrolidin-1-yl)-2-oxo-ethyl]-amide, 5-chloro-1H-indole-2-carboxylic acid [(1S)-benzyl-2-(3-hydroxy-azetidin-1-yl)-2-oxo-ethyl]-amide, 5-chloro-1H-indole-2-carboxylic acid [(1S)-benzyl-2-(3-hydroxyimino-azetidin-1-yl)-2-oxo-ethyl]-amide or 5-chloro-1H-indole-2-carboxylic acid [(1S)-benzyl-2-(4-hydroxyimino-piperidin-1-yl)-2-oxo-ethyl]-amide.

In a second aspect, this invention provides novel compounds of Formula 4

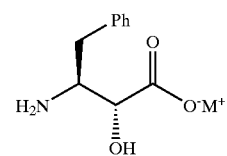

4 wherein $M^+$ is tetra-$C_1$–$C_6$ alkylammonium. A preferred embodiment of said second aspect is the novel compound of Formula 4a

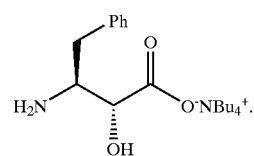

4a

In a third aspect, this invention provides novel compounds of Formula 5

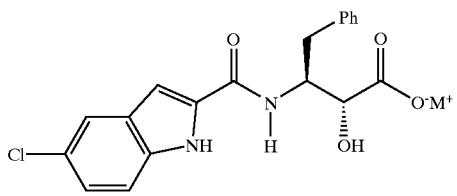

5 wherein $M^+$ is tetra-$C_1$–$C_6$ alkylammonium. A preferred embodiment of said second aspect is the novel compound of Formula 5a

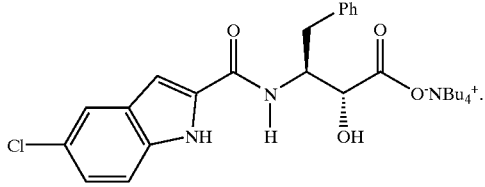

5a

This invention also includes, in yet another aspect, the scaling-up of the novel processes to provide commercial quantities of any of the compounds used and formed in these processes, including the starting materials, intermediates and final product. For example, the dropwise addition (preferably using an addition funnel) of a solution comprising the compound of Formula 2 to the mixture comprising the compound of Formula 4.

Those skilled in the art will fully understand the terms used herein in the specification and the appendant claims to describe the present invention; nonetheless, unless otherwise provided herein, the following terms are as described immediately below.

"Alkyl" means a straight or branched hydrocarbon chain radical, where "$C_1$–$C_6$ alkyl" includes methyl, ethyl, propyl, isopropyl, butyl, sec-butyl, tertiary butyl, pentyl, isopentyl, hexyl and isohexyl, and "$C_1$–$C_4$ alkyl" includes methyl, ethyl, propyl, isopropyl, butyl, secondary butyl, and tertiary butyl.

"Aprotic" means a solvent without an available proton.

"Protic" means a solvent with an available proton.

Unless otherwise noted, throughout this document and the appendant claims: % is percent, ACN is acetonitrile, °C. is degrees-Celsius, $CH_2Cl_2$ is methylene chloride, cm is centimeter or centimeters, DEC is 1-(3-dimethylaminopropyl)-3-ethylcarbodiimide hydrochloride, DMF is dimethylformamide, eq. or equiv. is equivalent or equivalents, EtOAc is ethyl acetate, g is gram or grams, h is hour or hours, HCl is hydrochloric acid, $HClO_4$ is perchloric acid, $H_2O$ is water, H2SO4 is sulfuric acid, HPLC is high performance liquid chromatography, $K_2CO_3$ is potassium carbonate, $K_3PO_4$ is tribasic potassium phosphate, M is molar (concentration), MeOH is methanol, $MgSO_4$ is magnesium sulfate, min is minute or minutes, mL is milliliter or milliliters, mm is millimeter or millimeters, mmol is millimole or millimoles, MS is mass spectrum, N is normal (concentration), $NaHCO_3$ is sodium bicarbonate, NaOH is sodium hydroxide, $NBu_4^+$ is tetrabutylammonium or TBA, nm is nanometer or nanometers, NMR is proton nuclear magnetic resonance spectrum, RP-HPLC is reversed-phase HPLC, RT is room temperature, TBAB is tetrabutylammonium bromide, THF is tetrahydrofuran, µL is microliter or microliters, µm is micromole or micromoles, UV is ultraviolet, and v/v is volume/volume.

DETAILED DESCRIPTION OF THE INVENTION

This invention provides novel processes for preparing the compound of Formula 6 from the compounds of Formulae 1 and 3. These starting materials are known compounds which can be prepared by those skilled in the art. In addition, both of these compounds are commercially available as described in more detail below in the EXAMPLES.

The compound of Formula 2 can be prepared by placing the compound of Formula 1 in any suitable aprotic solvent, preferably toluene, adding (preferably dropwise) any suitable activating agent for preparing an acid chloride, preferably $SOCl_2$, and then adding any suitable catalytic aprotic solvent, preferably DMF. This solution comprising the compound of Formula 2 can then be added directly to a solution comprising the compound of Formula 4. Alternatively, and preferably, the compound of Formula 2 can be first isolated by adding any suitable insolubilizing solvent, preferably hexanes, to the solution comprising the compound of Formula 2, filtering the solution and then drying the retentate. The isolated compound of Formula 2 can then be dissolved in any suitable aprotic solvent, preferably THF, and added to the solution comprising the compound of Formula 4.

The compound of Formula 4 can be prepared by adding the compound of Formula 3 and any suitable base, preferably $K_3PO_4$, to a mixture of any suitable aprotic solvent, preferably THF, and any suitable protic solvent, preferably $H_2O$, at RT under any suitable inert gas, preferably $N_2$, and the resultant slurry can be cooled, preferably in a mixture of ice in acetone. The immediately aforementioned base is provided to maintain the pH at from about pH 8 to about pH 13, preferably from about pH 11 to about pH 13.

The solution comprising the compound of Formula 2 can then be added, under any suitable inert gas, preferably $N_2$, over any suitable period of time, preferably from about 1 h to about 2 h, with cooling maintained throughout the addition, followed by continued cooling for any suitable period of time, preferably from about 1 to about 2 h, then warming to RT, to isolate the compound of Formula 5.

The compound of Formula 6 can then be prepared from the compound of Formula 5 by adding any suitable aprotic solvent, preferably $CH_2Cl_2$, separating the aqueous and organic layers, washing the organic layer with an aqueous acid, preferably HCl, preferably 1M HCl, concentrating the washed organic layer, preferably by distillation, displacing the concentrated organic layer into any suitable organic liquid, preferably heptanes, cooling to RT over any suitable period of time, e.g., overnight, filtering the resultant slurry and drying the resultant solid or retentate, i.e., the compound of Formula 6, under a vacuum over any suitable period of time, e.g., overnight.

Verification that the novel processes provided by this invention provide the compound of Formula 6 can be readily conducted by those skilled in the art. The presence of the compound of Formula 6 in, as well as the relative and absolute purity of, the resultant dried down solid can be determined by HPLC, specifically by HPLC UV area %, and by comparison with an external standard. The chemical structure of the resultant compound of Formula 6 can be verified by mass and NMR spectroscopy.

As those skilled in the art will appreciate, any suitable amounts of any of the materials used in the novel processes of this invention can be used therein, depending upon, for example, the desired amount of 3(S)-[(5-chloro-1H-indole-2-carbonyl)-amino]-2(R)-hydroxy-4-phenyl-butyric acid.

However, more particularly, in the step of preparing the compound of Formula 2, the amounts of the aprotic solvent A, the catalytic aprotic solvent and the activating agent are based on the amount of the compound of Formula 1:

for the aprotic solvent A—from about 4 mL/g of the compound of Formula 1 to about 30 mL/g of the compound of Formula 1 is preferred, from about 7 mL/g to about 20 mL/g is particularly preferred, and about 10 mL/g is most preferred;

for the catalytic aprotic solvent—from about 0.0001 mL/g of the compound of Formula 1 to about 0.25 mL/g of the compound of Formula 1 is preferred, from about 0.002 mL/g to about 0.1 mL/g is particularly preferred, and about 0.0004 mL/g is most preferred;

for the activating agent—from about 0.95 moles/mole of the compound of Formula 1 to about 2.0 moles/mole of the compound of Formula 1 is preferred, from about 1.1 moles/mole to about 1.5 moles/mole is particularly preferred, and about 1.3 moles/mole is most preferred.

Likewise, in the step of preparing the compound of Formula 4, the amounts of the base, aprotic solvent B, and the protic solvent are based on the amount of the compound of Formula 3:

for the base—from about 1.9 moles/mole of the compound of Formula 3 to about 3.0 moles/mole of the compound of Formula 3 is preferred, from about 2.0 moles/mole to about 2.3 moles/mole is particularly preferred, and about 2.1 moles/mole is most preferred;

for the aprotic solvent B—from about 3 mL/g of the compound of Formula 3 to about 30 mL/g of the compound of Formula 3 is preferred, from about 4 mL/g to about 10 mL/g is particularly preferred, and about 5 mL/g is most preferred;

for the protic solvent—from about 3 mL/g of the compound of Formula 3 to about 30 mL/g of the compound of Formula 3 is preferred, from about 4 mL/g to about 10 mL/g is particularly preferred, and about 5 mL/g is most preferred.

Further yet, in the step of adding the organic solvent, the amount of the organic solvent is based on the amount of the compound of Formula 3, i.e., from about 3 mL/g of the compound of Formula 3 to about 30 mL/g of the compound of Formula 3 is preferred, from about 4 mL/g to about 10 mL/g is particularly preferred, and about 5 mL/g is most preferred.

As discussed above, novel intermediates are generated in the novel processes provided by this invention. First in time are the novel intermediates of Formula 4 where $M^+$ is tetra-$C_1$–$C_6$ alkylammonium prepared from the compound of Formula 3, followed by the novel intermediates formed from the coupling of the compound of Formula 4 and the compound of Formula 2 to provide the novel intermediates of Formula 5. Preferred intermediates include those of the aforementioned Formulae 4a and 5a wherein $M^+$ is $NBu_4^+$ (from, e.g., TBAB).

Those skilled in the art will understand, based upon this disclosure, how to readily prepare the novel compounds of Formulae 4, 4a, 5, and 5a using conventional synthetic methods. For example, the compound of Formula 4a can be prepared by adding the compound of Formula 3 and any suitable base, preferably $K_3PO_4$, to a mixture of any suitable aprotic solvent, preferably THF, and any suitable protic solvent, preferably $H_2O$, and tetrabutylammonium bromide, at RT, under any suitable inert gas, preferably $N_2$, and the resultant slurry cooled, preferably in a mixture of ice in acetone. The compound of Formula 2, prepared as discussed above, can then be added, as also discussed above, to this solution comprising the compound of Formula 4a, to provide the compound of Formula 5a. As described above for the compounds of Formulae 4 and 5, neither of the compounds of Formulae 4a and 5a need be isolated, and preferably are not, during the process of this invention prior to their respective next processing steps.

As those skilled in the art will appreciate from the present disclosure, depending upon, for example, the desired scale, where used in the novel processes, heat can be applied in any suitable manner, e.g., the use of a heating mantle is generally convenient. Likewise, any suitable method of cooling can be used in the processes of this invention, e.g., standing at RT, an ice bath, a cold room, or simply removing the heating source.

This invention also includes any geometric and optical isomers of these novel intermediates. Also included are isotopically-labeled compounds of Formulae 4a and 5a, which are identical to those recited in Formulae 4a and 5a, but for the fact that one or more atoms are replaced by an atom having an atomic mass or mass number different from the atomic mass or mass number usually found in nature. Examples of isotopes that can be incorporated into such novel intermediates of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

While not intending to be bound by any particular theory, those skilled in the art will appreciate that the carboxylate salt of the compound of Formula 3 renders the compound of Formula 3 more soluble in the aprotic solvent within which the coupling of the compound of Formula 2 with the compound of Formula 3 occurs. As those skilled in the art will also understand, such increased solubility of the compound of Formula 3 substantially eliminates unwanted hydrolysis of the compound of Formula 2 back to the compound of Formula 1 which would otherwise negatively impact upon the production of the compound of Formula 4, and thus, the yield of 3(S)-[(5-chloro-1H-indole-2-carbonyl)-amino]-2(R)-hydroxy-4-phenyl-butyric acid.

While the compound of Formula 6 provided by the novel processes of this invention can be further reacted to prepare compounds and derivatives disclosed in the aforementioned WO 96/39385 and/or WO 96/39384, the processes of this invention, by virtue of the formation of the carboxylate salt of the compound of Formula 3, avoid the steps of protecting and deprotecting the carboxylate group disclosed in the aforementioned WO 96/39385 and/or WO 96/39385. As those skilled in the art would understand, fewer overall steps and the use of intermediates which maintain their solubility, do not undergo appreciable self-dimerization or hydrolysis prior to the coupling, and need not be isolated before their subsequent coupling provide advantages which are particularly realized at commercial scale-up.

The present invention includes any suitable methods for preparing the compounds of Formulae 2 and 4 and, as such, those skilled in the art, based upon this disclosure, may choose to protect a particular functionality, e.g., to prevent interference by such functionality in reactions at other sites within the molecule or to preserve the integrity of such functionality, for any given case. The need for, and type of, such protection are readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991. Suitable protecting groups for any particular functionality would include those which are not substantially chemically reactive under the reaction conditions described for the novel processes and which can be removed without substantially chemically altering other functionalities of any given intermediate. As will be understood by those skilled in the art, the protecting group(s) can be removed as so desired in any given preparation method, e.g., in a subsequent step.

Those skilled in the art will understand, based upon this disclosure and the descriptions provided by the aforementioned WO 96/39385 and WO 96/39384, how to readily prepare the compounds of WO 96/39385 and WO 96/39384 from the compound of Formula 6 using conventional synthetic methods such as, for example, the aforementioned Procedure A disclosed therein, and provided immediately below.

Procedure A (Peptide Coupling Using DEC)

A solution of a primary amine (0.1–0.7M, 1.0 equiv., or a primary amine hydrochloride and 1.0–1.3 equiv. of triethylamine per equiv. HCl) in dichloromethane (or any suitable solvent) is treated sequentially at 25° C. with the specified carboxylic acid (0.95–1.2 equiv.), hydroxybenzotriazole hydrate (1.2–1.8 equiv., usually 1.5 equiv. relative to the carboxylic acid), and DEC (0.95–1.2 equiv., corresponding in mole ratio to the carboxylic acid), and the mixture is stirred for 14–20 h. (On larger scale couplings, e.g., >50 mL solvent, the mixture is concentrated at this point and the residue is dissolved in EtOAc). The mixture is diluted with EtOAc, washed 2–3 times with 1N or 2N NaOH, 2–3 times with 1N or 2N HCl (where the product contains an ionizable amine functionality, the acid is omitted), the organic layer is dried over $MgSO_4$, and concentrated giving crude product which is purified by chromatography on silica gel, trituration, or recrystallization, with suitable solvents. Purified products are analyzed by RP-HPLC. Reactions conducted at 0° C. to 25° C. are conducted with an initial cooling of the vessel in an insulated ice bath which is allowed to warm to RT over several h. Those skilled in the art will understand (e.g., from the description in the aforementioned WO 96/39385 and WO 96/39384) how to modify Procedure A depending, for example, on the ultimate compound sought to be prepared from the compound of Formula 6, and such modifications are considered part of this invention.

The present invention is illustrated by the following EXAMPLES which are provided solely for the purposes of illustration and do not limit the invention. Moreover, it will also be understood that other changes and modifications that may be practiced are also part of this invention and, as such, are also within the scope of the appendant claims: those skilled in the art will recognize, or be able to ascertain without undue experimentation, equivalents to the specific embodiments of this invention described herein, and such equivalents are intended to be encompassed by the appendant claims.

In the EXAMPLES, the identity and the purity evaluation of the product of the novel processes of this invention were provided by RP-HPLC analysis. More particularly, RP-HPLC analysis was performed using a Waters (34 Maple Street, Milford, Mass. 01757) Symmetry C8, 5 $\mu$m, 15 cm length×3.9 mm I.D., column temperature of 40° C., Mobile Phase A [800:200:4, deionized $H_2O$:MeOH:$HClO_4$, v/v] was prepared, for 1L, by mixing 800 mL deionized $H_2O$, 200 mL MeOH, and 4 mL $HClO_4$ and degassing under a vacuum [where volumes of components can be adjusted to prepare appropriate volumes, for any given case], Mobile Phase B [800:200 ACN:MeOH, v/v] was prepared, for 1L, by mixing 800 mL ACN and 200 mL MeOH, and degassing under a vacuum [where volumes of components can be adjusted to prepare appropriate volumes, for any given case], the solvents are continually degassed by purging with helium or by using an in-line degasser, detection at UV 220 nm, flow rate of 2.0 mL/min, injection volume of 20 $\mu$L, runtime of 65 min [including a reequilibration between injections]. The retention time of 3(S)-[(5-chloro-1H-indole-2-carbonyl)-amino]-2(R)-hydroxy-4-phenyl-butyric acid is approximately 15 min under these chromatographic conditions.

The compound of Formula 1 used in the EXAMPLES was purchased from Merck SA. (Zone Iuindustrielle 45300, Tithivier, France).

The compound of Formula 3 used in the EXAMPLES was purchased from Nippon Kayaku. (Fujimi Building, 11-2 Fujimi 1-Chone, Chiyoda-Ka 102, Japan).

EXAMPLES

Example 1

Preparation of the Compound of Formula 2

A. Wherein the activating agent is thionyl chloride.

The compound of Formula 1 [50.00 g, 255.6 mmol] was added to toluene [500 mL]. DMF [0.02 mL, 0.2556 mmol, (0.001 eq.)] was added. The slurry was stirred under $N_2$. Thionyl chloride [24.24 mL, 332.3 mmol, (1.30 eq.)] was added dropwise, and then the mixture was heated to 85° C., and reacted for about 18 h. The solution was cooled to 40° C. and concentrated by vacuum distillation to about 100–150 mL at which time the vacuum was broken and hexanes [250 mL] were added dropwise over about 1 h at 40° C. The slurry was then allowed to cool to RT and was stirred, granulated, filtered and dried. The yield of the compound of Formula 2 was 51.98 g [solid, 95%].

B. Wherein the activating agent is oxalyl chloride.

Oxalyl chloride [4.6 mL, 53.8 mmol, (1.05 eq.)] was added to a slurry of the compound of Formula 1 [10.0 g, 51.3 mmol, (1.0 eq.)] in $CH_2Cl_2$ [200 mL]. A couple of drops of DMF were then added slowly. After the gas evolution had subsided, additional DMF [10 mL] was added, and the solution was stirred until it was homogeneous.

Example 2

Preparation of the Compound of Formula 4

A. Wherein $M^+$ is $K^+$.

The compound of Formula 3 [5.00 g, 25.6 mmol] and $K_3PO_4$ [11.42 g, 53.8 mmol, (2.10 eq.)] were stirred in THF (25 mL) and $H_2O$ (25 mL) at RT. The solution was then cooled to about −5° C.

B. Wherein $M^+$ is $Na^+$.

The compound of Formula 3 [75.00 g, 384.2 mmol] was stirred in THF [375 mL] and $H_2O$ [375 mL]. $NaHCO_3$ [80.68 g, 960.5 mmol, (2.50 eq.)] was added. The slurry was then stirred and heated to about 65° C. to develop a clear solution.

C. Wherein $M^+$ is $NBu_4+$.

1. Methanol [200 mL] was added to the compound of Formula 3 [10.0 g, 51.3 mmol, (1.0 eq.)], followed by $K_2CO_3$ [7 g, 51.3 mmol, (1.0 eq.), finely ground], which was followed by TBAB [17.0 g, 51.3 mmol, (1.0 eq.)]. The slurry was stirred until it was free flowing. Methylene chloride [100 mL] was then added, followed by $KHCO_3$ [20.0 g, 20 mmol, (4 eq.), finely ground].

2. Water [20 mL] and $CH_2Cl_2$ [200 mL] were added to the compound of Formula 3 [10.0 g, 51.3 mmol, (1.0 eq.)], followed by $K_2CO_3$ [35 g, 256 mmol, (5.0 eq.], which was followed by TBAB [17.0 g, 51.3 mmol, (1.0 eq.)]. The slurry was stirred until it was free flowing.

Example 3

Coupling, Termination and Isolation, and Analyses

A. The compound of EXAMPLE 1.A. with the compound of EXAMPLE 2.A.

1. Coupling.

An amount of the compound of EXAMPLE 1.A. [5.47 g, 25.6 mmol] was dissolved in THF [25 mL]. This solution was then added to the solution prepared in EXAMPLE 2.A. over a period of 80 min at −5° C. The resultant slurry was stirred for about 2 h at −5° C. and allowed to warm to RT.

2. Termination and Isolation.

Methylene chloride [25 mL] was added to the completed coupling reaction and the mixture was stirred for 15 min.

The aqueous and organic layers were then separated. The organic layer was treated with 1 M HCl [2×25 mL]. The acid treated organic layer was then concentrated by distillation and displaced into heptanes by gradual addition of the heptanes until the vapor temperature reached 95° C., and then cooled to ambient temperature. The resultant slurry was filtered and the solid dried in a vacuum oven. The yield of 3(S)-[(5-chloro-1H-indole-2-carbonyl)-amino]-2(R)-hydroxy-4-phenyl-butyric acid was 9.16 g (solid, 96.0%).

3. Analyses.

a. The solid appeared greater than 99% pure by HPLC UV area %.

b. 1H NMR (400 Mhz, CDCl$_3$/DMSO-d$_6$) δ10.99 (s, 1H, NH), 7.61 (d, 1H, NH), 6.82–7.34 (m, 9H), 4.63–4.69 (m, 1H, C$_3$H), 3.99–4.00 (m, 1H, C$_2$H), 2.84–2.95 (m, 2H, C$_4$H).

c. MS (M−1)=371 for C$_{19}$H$_{17}$ClN$_2$O$_4$.

B. The compound of EXAMPLE 1.A. with the compound of EXAMPLE 2.B.

1. Coupling.

The compound of Formula 2 prepared in the same overall manner as described in EXAMPLE 1.A. [82.24 g, 384.2 mmol] was dissolved in THF [190 mL]. This solution was then added to the solution prepared in EXAMPLE 2.B. over a period of 50 min at 65° C. The resultant slurry was stirred for about 3.5 h at 65° C. and allowed to cool to RT.

2. Termination and Isolation.

Ethyl acetate [375 mL] was added to the completed coupling reaction. The resultant mixture was stirred and then allowed to settle. The aqueous and organic layers were then separated. The organic layer was treated with 1 M HCl [375 mL] and H$_2$O [375 mL]. The aqueous and organic layers were then separated. The organic layer was then concentrated by distillation. The EtOAc/THF mixture was concentrated and removed while replacing with heptanes [375 mL]. The resultant slurry was granulated, filtered and dried in a vacuum oven. The yield of 3(S)-[(5-chloro-1 H-indole-2-carbonyl)-amino]-2(R)-hydroxy-4-phenyl-butyric acid was 132.34 g (solid, 92.4%).

3. Analyses.

The solid appeared pure by HPLC UV area %, and gave the same NMR and MS data as provided in EXAMPLE 3.A.

C. The compound of EXAMPLE 1.B. with the compound of EXAMPLE 2.C.1.

1. Coupling.

The solution of EXAMPLE 1.B. was added to the solution of EXAMPLE 2.C.1. dropwise using an addition funnel over a period of 2 h. After one quarter of the solution of the compound of Formula 2 had been added, K$_2$CO$_3$ [7.0 g, 51.3 mmol, (1.0 eq.), finely ground] was added. After three quarters of the solution of the compound of Formula 2 had been added, K$_2$CO$_3$ [7.0 g, 51.3 mmol, (1.0 eq.), finely ground] was added. The pH of the reaction was determined prior to the addition of the compound of Formula 2 [pH 11] and at the end of addition [pH 9], by taking a pH strip and dipping it directly into the reaction mixture.

2. Termination and Isolation.

The completed coupling reaction was filtered to remove inorganic salts [the cake was washed with MeOH until HPLC showed no product], diluted with EtOAc, and the volatiles removed in vacuo. The EtOAC layer [about 500 mL] was then washed 3 times with 1M H$_2$SO$_4$ [100 mL, ice cold]. To ensure that the TBA salts were removed, an aliquot was stripped and analyzed by NMR. This was followed by 2 washes with brine [100 mL], drying with sodium sulfate, filtration, and concentration in vacuo. The product was concentrated to about 100 mL of EtOAc and precipitated upon the addition of hexane [about 100 mL]. The slurry was stirred overnight and then filtered. The yield of 3(S)-[(5-chloro-1H-indole-2-carbonyl)-amino]-2(R)-hydroxy-4-phenyl-butyric acid was 16.62 g [solid, 87%].

3. Analyses.

The solid appeared greater than 99.5% pure by HPLC UV area %, and gave the same NMR and MS data as provided in EXAMPLE 3.A.

D. The compound of EXAMPLE 1.B. with the compound of EXAMPLE 2.C.2

1. Coupling.

The solution of EXAMPLE 1.B. was added to the mixture of EXAMPLE 2.C.2. dropwise using an addition funnel over a period of 2 h. The pH of the slurry was about pH 11 throughout [determined by taking a pH strip and dipping it directly into the reaction mixture]. The reaction mixture was diluted with MeOH and the CH$_2$Cl2 removed in vacuo. The pH was adjusted to pH 13–14 with 1N NaOH and stirred overnight.

2. Termination and Isolation.

The reaction mixture was diluted with EtOAc, and the volatiles removed in vacuo. The mixture [containing about 500 mL of EtOAc] was brought to pH 1 with 6M HCl. The EtOAC layer was separated and then washed twice with 1M HCl. This was followed by 2 washes with brine [100 mL], drying with sodium sulfate, filtration, and concentration in vacuo. The product was concentrated to about 100 mL of EtOAc and precipitated upon the addition of hexanes [about 100 mL]. The slurry was stirred overnight and then filtered. The yield of 3(S)-[(5-chloro-1H-indole-2-carbonyl)-amino]-2(R)-hydroxy-4-phenyl-butyric acid was 16.59 g [solid, 87%].

3. Analyses.

The solid appeared greater than 98% pure by HPLC UV area %, and gave the same NMR and MS data as provided in EXAMPLE 3.A.

What is claimed is:

1. A process for preparing the compound of Formula 6 comprising the steps of:

preparing a solution comprising the compound of Formula 2, comprising, in sequence, adding to the compound of Formula 1 from about 4 mL/g of said compound of Formula 1 to about 30 mL/g of said compound of Formula 1 of an aprotic solvent A, adding an amount of from about 0.0001 mL/g of said compound of Formula 1 to about 0.25 mL/g of said compound of Formula 1 of a catalytic aprotic solvent with agitation under an inert gas, and adding from about 0.95 moles/mole of said compound of Formula 1 to about 2.0 moles/mole of said compound of Formula 1 of an activating agent;

preparing a compound of Formula 4 comprising, in sequence, adding the compound of Formula 3 and from about 1.9 moles/mole of said compound of Formula 3 to about 3.0 moles/mole of said compound of Formula 3 of a base to a mixture of from about 3 mL/g of said compound of Formula 3 to about 30 mL/g of said compound of Formula 3 of an aprotic solvent B and from about 3 mL/g of said compound of Formula 3 to about 30 mL/g of said compound of Formula 3 of a protic solvent, at a temperature of from about −20° C. to about the reflux temperature of said mixture, and maintaining the pH of said mixture at from about pH 8 to about pH 13;

preparing a compound of Formula 5 comprising, in sequence, adding said solution to said mixture, under said inert gas, while maintaining said temperature and, after said addition is complete, allowing said mixture to reach room temperature;

adding an amount of from about 3 mL/g of said compound of Formula 3 to about 30 mL/g of said compound of Formula 3 of an organic solvent to said mixture; and extracting said compound of Formula 6 into said organic solvent comprising, in sequence, separating the aqueous layer A and the organic layer A, treating said organic layer A with an aqueous acid solution, or with an aqueous acid solution and $H_2O$, separating the aqueous layer B from the organic layer B, and retaining said organic layer B; wherein:

$M^+$ is any monovalent cation, provided that, where $M^+$ is $N(C_1-C_6\ alkyl)_4^+$, tetra-$C_1$-$C_6$ ammonium halide is added to said mixture after said base;

said compound of Formula 1 is

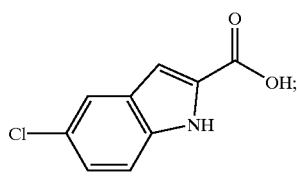

1 said compound of Formula 2 is

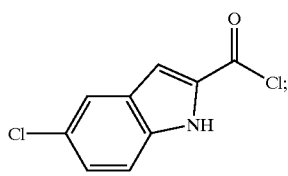

2 said compound of Formula 3 is

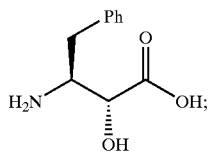

3 said compound of Formula 4 is

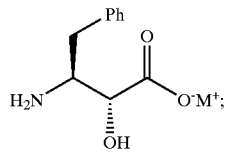

4 said compound of Formula 5 is

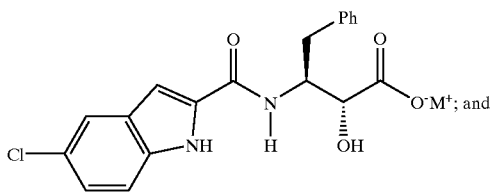

5 and
said compound of Formula 6 is

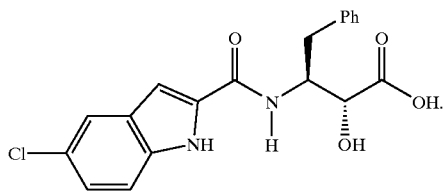

6

2. The process as defined in claim 1 wherein said aprotic solvent A and said aprotic solvent B are each independently THF, toluene, or $CH_2Cl_2$.

3. The process as defined in claim 1 wherein said catalytic aprotic solvent is DMF.

4. The process as defined in claim 1 wherein said inert gas is $N_2$.

5. The process as defined in claim 1 wherein said activating agent is oxalyl chloride or thionyl chloride.

6. The process as defined in claim 1 wherein $M^+$ is $Li^+$, $Na^+$, $K^+$, $Cs^+$ or tetra-$C_1$-$C_6$ alkylammonium.

7. The process as defined in claim 6 wherein $M^+$ is $Na^+$, $K^+$, or $NBu_4^+$.

8. The process as defined in claim 1 wherein said base is sodium bicarbonate, sodium hydroxide, sodium phosphate, potassium carbonate, dibasic potassium phosphate, or tribasic potassium phosphate.

9. The process as defined in claim 8 wherein said base is sodium bicarbonate, said $M^+$ is $Na^+$, said aprotic solvent B is THF, said protic solvent is $H_2O$, and said temperature is about 65° C.

10. The process as defined in claim 8 wherein said base is potassium carbonate, said $M^+$ is $NBu_4+$, and said tetra-$C_1$-$C_6$ alkylammonium halide is TBAB.

11. The process as defined in claim 8 wherein said $M^+$ is $K^+$, said aprotic solvent B is THF, said protic solvent is $H_2O$, and said temperature is about −5° C.

12. The process as defined in claim 1 wherein said protic solvent is $H_2O$ or ROH where R is $C_1-C_4$ alkyl.

13. The process as defined in claim 1 wherein said pH is maintained by said base.

14. The process as defined in claim 13 wherein said pH is from about pH 11 to about pH 13.

15. The process as defined in claim 1 wherein said organic solvent is EtOAc or $CH_2Cl_2$.

16. The process as defined in claim 1 wherein said aqueous acid solution is aqueous HCl or aqueous $H_2SO_4$.

17. The process as defined in claim 1 wherein said retained organic layer B is concentrated, displaced into hexanes or heptanes, granulated in said hexanes or said heptanes for a period of time under an inert gas, and the resultant slurry is filtered and the retenate (comprising the compound of Formula 6) is dried.

18. The process as defined in claim 1 wherein said compound of Formula 2 is isolated before its addition to said mixture, dissolved in an aprotic solvent C, and added to said mixture by adding said aprotic solvent C comprising said compound of Formula 2 to said mixture.

19. The process as defined in claim 18 wherein said isolating comprises, in sequence, adding hexanes or heptanes to said solution, filtering the resultant slurry and drying the retentate.

20. The process as defined in claim 18 wherein said aprotic solvent C is THF, toluene, or $CH_2Cl_2$.

21. The process as defined in claim 1 comprising the steps of: preparing a solution comprising the compound of Formula 2 comprising, in sequence, adding the compound of Formula 1 to toluene, adding an amount of DMF with stirring under $N_2$, and adding $SOCl_2$; preparing the compound of Formula 4 wherein $M^+$ is $Na^+$ from the compound of Formula 3 comprising, in sequence, adding said compound of Formula 3 and $NaHCO_3$ to a mixture of THF and $H_2O$, at about 65° C.; preparing the compound of Formula 5 wherein $M^+$ is $Na^+$ by coupling said compounds of Formulae 2 and 4 comprising, in sequence, adding said solution to said mixture, under $N_2$, while maintaining about 65° C. and, after said addition is complete, allowing said mixture to reach room temperature; adding an amount of EtOAc to said mixture; extracting said compound of Formula 6 into said EtOAc comprising, in sequence: separating said aqueous layer A and said organic layer A, treating said organic layer A with an aqueous acid solution, separating said aqueous layer B from said organic layer B, and retaining said organic layer B; and isolating said compound of Formula 6 comprising, in sequence: concentrating said retained organic layer B, displacing said concentrated organic layer B into hexanes or heptanes, granulating said displaced organic layer B in said hexanes or heptanes overnight under $N_2$, filtering the resultant slurry, and drying the retentate.

22. The process as defined in claim 1 comprising the steps of: preparing a solution comprising the compound of Formula 2 comprising, in sequence, adding the compound of Formula 1 to toluene, adding an amount of DMF with stirring under $N_2$, and adding $SOCl_2$; preparing the compound of Formula 4 wherein $M^+$ is $K^+$ from the compound of Formula 3 comprising, in sequence, adding said compound of Formula 3 and $K_3PO_4$ to a mixture of THF and $H_2O$, at about −5° C.; preparing the compound of Formula 5 wherein $M^+$ is $K^+$ by coupling said compounds of Formulae 2 and 4 comprising, in sequence, adding said solution to said mixture, under $N_2$, while maintaining about −5° C. and, after said addition is complete, allowing said mixture to reach room temperature; adding an amount of $CH_2Cl_2$ to said mixture; extracting said compound of Formula 6 into said $CH_2Cl_2$ comprising, in sequence: separating said aqueous layer A and said organic layer A, treating said organic layer A with 1M HCl, separating said aqueous layer B from said organic layer B, and retaining said organic layer B; and isolating said compound of Formula 6 comprising, in sequence: concentrating said retained organic layer B by distillation, displacing said concentrated layer into heptanes or hexanes until the vapor temperature reaches about 95° C., cooling to ambient temperature, filtering the resultant slurry, and drying the retentate.

\* \* \* \* \*